US00PP07903P

United States Patent [19]

van Andel

[11] Patent Number: Plant 7,903

[45] Date of Patent: Jul. 7, 1992

[54] CARNATION NAMED STAROTANG

[75] Inventor: Jacob van Andel, Aalsmeer, Netherlands

[73] Assignee: Van Staaveren B.V., Aalsmeer, Netherlands

[21] Appl. No.: 578,472

[22] Filed: Sep. 7, 1990

[51] Int. Cl.[5] ..... A01H 5/00

[52] U.S. Cl. ..... Plt./73.1

[58] Field of Search ..... Plt./70, 73

*Primary Examiner*—Howard J. Locker

*Attorney, Agent, or Firm*—Charles W. Rummler

[57] ABSTRACT

A new and original carnation cultivar particularly distinguished by its continuously-blooming, bright red blossoms, which are borne on tall, erect canes, the size of the plant itself averaging about 60 cm.

1 Drawing Sheet

BACKGROUND OF THE NEW PLANT

This new carnation cultivar originated as a hybrid seedling developed by me in 1985 at our nursery in Aalsmeer, Holland by crossing two varieties selected from our collection of carnations maintained for breeding purposes at Aalsmeer. This particular seedling was selected for propagation because of its bright red coloration and the overall high quality of the plant. Asexual propagation of this plant was done by means of cuttings under my direction at Aalsmeer and propagation of this new plant by cuttings was continued from generation to generation to determine whether the novel characteristics of the selected seedling would hold true from generation to generation so that its homogeneity could be assured.

This proved to be successful and this new carnation variety is now being propagated at Aalsmeer.

DESCRIPTION OF THE DRAWING

My new carnation cultivar is illustrated by the accompanying photographic drawing, which shows blooming portions of flower stems, the color rendition being as nearly true to that herein specified as is reasonably possible to obtain by professional photographic procedures.

DESCRIPTION OF THE NEW PLANT

The following is a detailed description of my new carnation cultivar based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Seedling.

Parentage:

*Seed parent.*—Stan 82-15 (unpatented).

*Pollen parent.*—Lontarion — U.S. Plant Pat. No. 5,435.

Classification:

*Botanic.*—*Dianthus caryophyllus.*

*Commercial.*—Standard carnation.

Form: Tall, vigorous bush.

Height: Averaging 100–150 cm.

Main stem:

*Length.*—About 60 cm.

*Growth.*—Vigorous, upright and strong.

*Branching character.*—Several emitted from the ground at the base of the main stem.

Foliage:

*Number of leaves.*—Varies with season.

*Leaf size.*—Medium.

*Leaf shape.*—Long, pointed, and slightly curled. Margins: Entire. Texture: Leathery. Color: Both upper and under side are gray-green.

THE BUD

Size: Medium.

*Diameter.*—Averaging about 2 cm.

*Length.*—Averaging about 3 cm.

Shape: Ovoid.

Calyx:

*Shape.*—Cylindrical.

*Size.*—Normal.

*Splitting.*—The calyx rarely splits.

*Aspect.*—Smooth.

Flower stem:

*Character.*—Erect.

*Color.*—Gray-green.

*Length.*—Averaging about 60 cm.

THE FLOWER

Blooming habit: Continuous the year around.

Size of flower: Medium.

*Diameter.*—Averaging about 8 cm.

*Depth.*—Averaging about 3 cm.

Borne: Singly.

Shape:

*When first opening.*—High center.

*When mature.*—High center.

Petalage:

*Number of petals.*—About 30.

*Texture.*—Soft.

*Appearance.*—Velvety.

*Color.*—Both outer and inside petals of a solid, unblemished bright red. Body: 44 B. Base: 44 B. Reverse side: 44 B.

Flower stem:

*Length.*—Averaging about 60 cm.

Discoloration:

*After full bloom.*—None.

Persistence: The flowers hang on and dry.

Disease resistance: Resistant to *Fusarium oxysporum* as observed at Aalsmeer.

Lasting quality: Averaging about 14 days as a cut flower and 21 days on the plant.

REPRODUCTIVE ORGANS

Stamens:

*Number.*—Few — approximately 10.

*Arrangement.*—Petaloid.

*Anthers.*—Size: Average. Color: White/Yellow/-Brownish.

*Filaments.*—Length: 5 to 30 mm, in average. Color: 155 B.

*Pollen.*—Color: 27 A.

Pistils:

*Number.*—1.

*Styles.*—Length: About 35 mm. Color: 52 B.

*Stigmas.*—Color: 189 A/D.

Characteristics of ovaries: Egg-shaped and green.

I claim:

1. The new and distinctive carnation cultivar, substantially as herein shown and described, particularly characterized by its continuously-blooming bright red flowers, which are borne on strong, upright stems of a tall, vigorously growing bush.

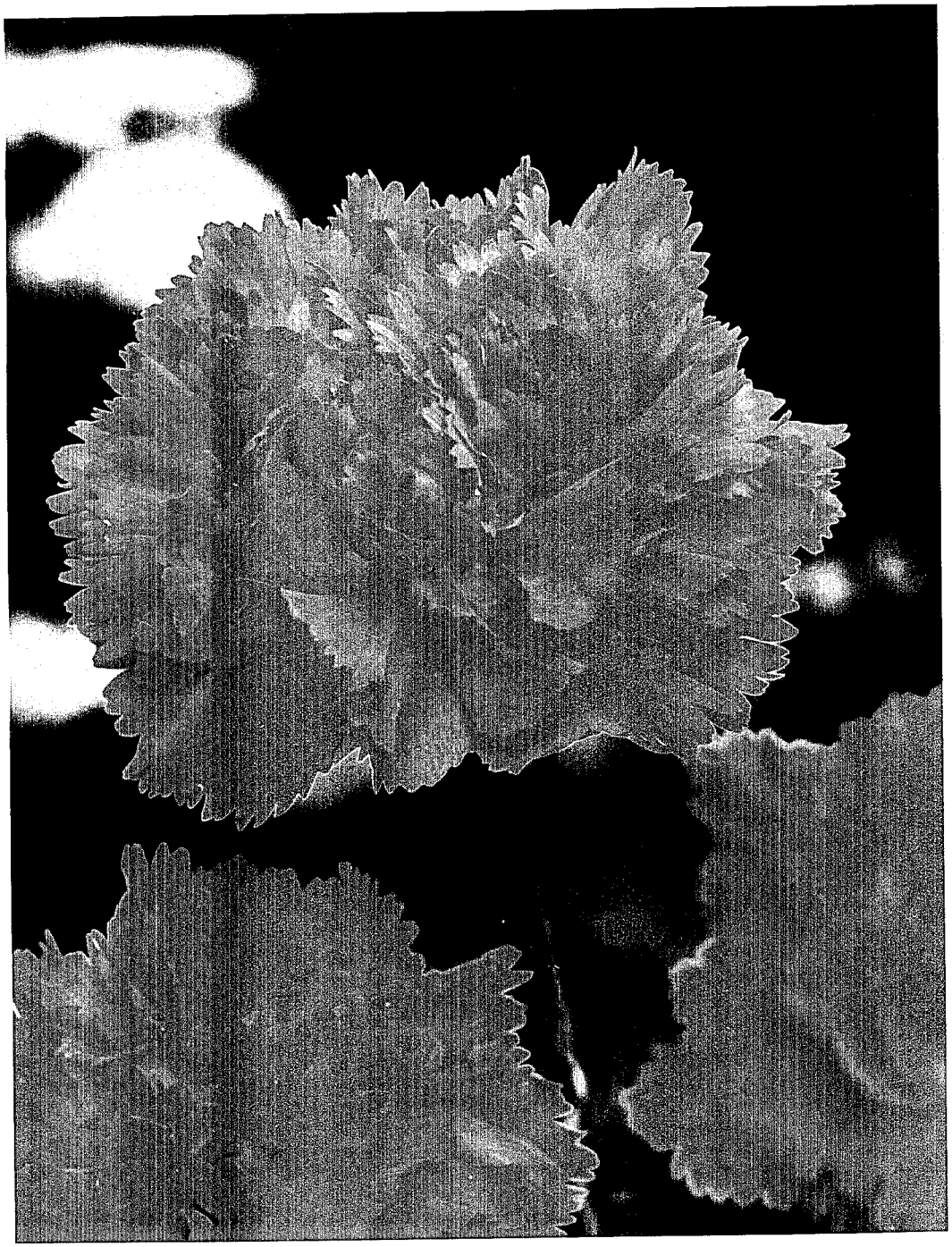

* * * * *